United States Patent
Golebiowski et al.

(10) Patent No.: US 6,872,825 B2
(45) Date of Patent: Mar. 29, 2005

(54) PEPTIDE β-TURN MIMETIC COMPOUNDS AND PROCESSES FOR MAKING THEM

(75) Inventors: Adam Golebiowski, Loveland, OH (US); Sean Rees Klopfenstein, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 447 days.

(21) Appl. No.: 10/149,874
(22) PCT Filed: Dec. 20, 2000
(86) PCT No.: PCT/US00/34832

§ 371 (c)(1),
(2), (4) Date: Jun. 14, 2002

(87) PCT Pub. No.: WO01/46197

PCT Pub. Date: Jun. 28, 2001

(65) Prior Publication Data

US 2003/0105103 A1 Jun. 5, 2003

Related U.S. Application Data

(60) Provisional application No. 60/172,823, filed on Dec. 21, 1999.

(51) Int. Cl.[7] .............................................. C07D 487/00
(52) U.S. Cl. ...................................... 544/350; 544/387
(58) Field of Search .................................. 544/350, 387

(56) References Cited

FOREIGN PATENT DOCUMENTS

WO    WO 97/15577 A1    5/1997
WO    WO 98/49168 A1    11/1998

OTHER PUBLICATIONS

Gillespie, P. et al., "Conformational Analysis of Dipeptide Mimetics", *Biopoly*, 1997, pp. 191–217, vol. 43.
Venkatachalam, C.M. et al., "Sterochemical Criteria for Polypeptides and Proteins. V. Conformation of a System of Three Linked Peptide Unites", *Biopolymers*, 1968, pp. 1425–1436, vol. 6.
Ball, J. B. et al., "β–Turn Topography", *Tetrahedron*, 1993, pp. 3467–3478, vol. 49, No. 17.
Kahn, M., "Peptide Secondary Structure Mimetics: Recent Advances and Future Challenges", *SYNLETT*, Nov. 1993, pp. 821–826.

Hanessian, S. et al., "Design and synthesis of conformationally Constrained Amino Acids as Versatile Scaffolds and Peptide Mimetics" *Tetradehron*, 1997, pp. 12789–12854, vol. 53, No. 38.

Golebiowski, A. et al., "Solid–Supported Synthesis of Peptide β–turn Mimetic", *Org. Letters*, 2000, pp. 2615–2617, vol. 2, No. 17.

Golebiowski, A. et al., "Solid Supported High–Throughput Organic Synthesis of Peptide β–Turn Mimetics Via Tandem Petasis Reaction/Diketopiperazine Formation", *Tetrahedron Letters*, Jun. 2000, pp. 4841–4844.

Senanayake C. H. et al., "Asymmetric synthesis of Conformationally Constrained cis–1–Amino–1–phenylclo-hexan–2–ol". *Tetrahedron*, May 1996, pp. 1501–1506, vol. 7, No. 5.

Primary Examiner—Bennett Celsa
Assistant Examiner—Jon D Epperson
(74) Attorney, Agent, or Firm—Richard S. Echler, Sr.; Mary Pat McMahon

(57) ABSTRACT

The subject invention involves compounds having structure (I), wherein: (a) R1 is hydrogen or alkyl; and R2 is selected from hydrogen, alkyl, aryl, heterocyclyl, carboxy and its esters and amides; or R1 and R2 are attached and are together alkylene or heteroalkylene; (b) R4 is selected from aryl, heteroaryl, and α,β-unsaturated conjugated aryl or heteroaryl; and (c) R5 is selected from hydrogen, alkyl, aryl, and heterocyclyl; and an optical isomer, diesteriomer, or enantiomer thereof; a salt, hydrate, ester, amide or imide thereof. The subject invention also includes libraries of such compounds, and processes for making the subject compounds and libraries.

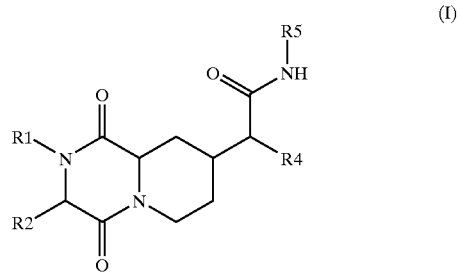

(I)

15 Claims, No Drawings

PEPTIDE β-TURN MIMETIC COMPOUNDS AND PROCESSES FOR MAKING THEM

CROSS REFERENCE

This application claims priority under Title 35, United States Code 119(e) from Provisional Application Ser. No. 60/172,823, filed Dec. 21, 1999.

FIELD OF THE INVENTION

The subject invention relates to novel peptide β-turn mimetic compounds and processes for making such compounds.

BACKGROUND

In peptides, the β-turn is a subset of the reverse turn and is a common feature of biologically active peptides and proteins; it is widely thought to act as a molecular recognition site for many biological processes. Specific types of β-turns are classified according to their geometry.

The b-turn is defined as any tetrapeptide sequence with a 10-membered intramolecularly H-bonded ring, in which the $C_a^i$ to $C_a^{i+3}$ distance varies from 4 to 7 Å.

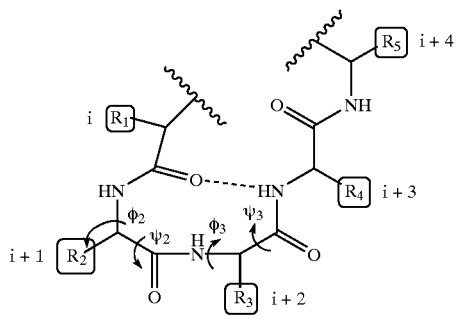

Depending on $f_2$, $y_2$, $f_3$ and $y_3$ there are many types of b-turn structures described in literature. (See: Gillespie et al., "Conformational Analysis of Dipeptide Mimetics", Biopoly, Vol. 43, (1997), pp. 191–217; Venkatachalam, Biopolymers, Vol. 6, (1968), pp. 1425–36.

The subject invention compounds are mimetics for β-turn peptides. Such compounds are useful as probes for the study of molecular recognition events, including enzyme inhibition, cell-cell and cell-matrix interactions. One physical consequence of such conformational constraint of the subject compounds is a limiting of the number of accessible conformational states of the molecules, leading to a better definition of the bioactive conformation of corresponding active peptides.

Information regarding β-turn peptides and mimetic compounds can also be found, for example, in the following references: Ball et al., "β-Turn Topography", Tetrahedron, Vol. 49, No. 17 (1993), pp. 3467–3478; Kahn, "Peptide Secondary Structure Mimetics: Recent Advances and Future Challenges", SYNLETT, (November 1993), pp. 821–826; Hanessian et al., "Design and Synthesis of Conformationally Constrained Amino Acids as Versatile Scaffolds and Peptide Mimetics", Tetrahedron, Vol. 53, No. 38 (1997), pp. 12789–12854.

SUMMARY OF THE INVENTION

The subject invention includes compounds having the structure:

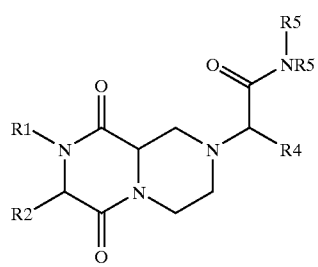

wherein:
(a) R1 is hydrogen or alkyl; and R2 is selected from hydrogen, alkyl, aryl, heterocyclyl, carboxy and its esters and amides; or R1 and R2 are attached and are together alkylene or heteroalkylene;
(b) R4 is selected from aryl, heteroaryl, and α,β-unsaturated conjugated aryl or heteroaryl; and
(c) each R5 is independentlyselected from hydrogen, alkyl, aryl, and vo R5 units can be taken together to form a heterocyclic ring.

and an optical isomer, diesteriomer, or enantiomer thereof; a salt, hydrate, ester, amide, or imide thereof.

The subject invention also includes libraries of such compounds, and processes for making the subject compounds and libraries.

DETAILED DESCRIPTION OF THE INVENTION

As used herein unless specified otherwise, "alkyl" means a hydrocarbon chain which is branched, linear or cyclic, saturated or unsaturated (but not aromatic), substituted or unsubstituted. The term "alkyl" may be used alone or as part of another word where it may be shortened to "alk" (e.g., in alkoxy, alkylacyl). Preferred linear alkyl have from one to about twenty carbon atoms, more preferably from one to about ten carbon atoms, more preferably still from one to about six carbon atoms, still more preferably from one to about four carbon atoms; most preferred are methyl or ethyl. Preferred cyclic and branched alkyl have from three to about twenty carbon atoms, more preferably from three to about ten carbon atoms, more preferably still from three to about seven carbon atoms, still more preferably from three to about five carbon atoms. Preferred cyclic alkyl have one hydrocarbon ring, but may have two, three, or more, fused or spirocycle hydrocarbon rings. Preferred alkyl are unsaturated with from one to about three double or triple bonds, preferably double bonds; more preferably they are mono-unsaturated with one double bond. Still more preferred alkyl are saturated. Saturated alkyl are referred to herein as "alkanyl". Alkyl unsaturated only with one or more double bonds (no triple bonds) are referred to herein as "alkenyl". Preferred substituents of alkyl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, nitro, and cyano. Also, unsubstituted alkyl are preferred.

As used herein, "heteroatom" means a nitrogen, oxygen, or sulfur atom.

As used herein, "alkylene" means an alkyl which connects two other moieties, "heteroalkylene" means an alkylene having one or more heteroatoms in the connecting chain.

As used herein unless specified otherwise, "aryl" means an aromatic hydrocarbon ring (or fused rings) which is substituted or unsubstituted. The term "aryl" may be used alone or as part of another word (e.g., in aryloxy, arylacyl). Preferred aryl have from six to about fourteen, preferably to about ten, carbon atoms in the aromatic ring(s), and a total of from about six to about twenty, preferably to about twelve, carbon atoms. Preferred aryl is phenyl or naphthyl; most preferred is phenyl. Preferred substituents of aryl include halo, alkyl, aryl, heterocycle, hydroxy, alkoxy, aryloxy, thio, alkylthio, arylthio, amino, alkylamino, arylamino, amide, alkylamide, arylamide, formyl, alkylacyl, arylacyl, carboxy and its alkyl and aryl esters and amides, nitro, and cyano. Also, unsubstituted aryl are preferred.

As used herein unless specified otherwise, "heterocycle" or "heterocyclyl" means a saturated, unsaturated or aromatic cyclic hydrocarbon ring (or fused rings) with one or more heteroatoms in the hydrocarbon ring(s). Preferred heterocycles have from one to about six heteroatoms in the ring(s), more preferably one or two or three heteroatoms in the ring(s). Preferred heterocycles have from three to about fourteen, preferably to about ten, carbon plus heteroatoms in the ring(s), more preferably from three to about seven, more preferably still five or six, carbon plus heteroatoms in the rings(s); and a total of from three to about twenty carbon plus heteroatoms, more preferably from three to about ten, more preferably still five or six, carbon plus heteroatoms. Preferred heterocycles have one ring, but may have two, three, or more, fused or spirocycle rings. More preferred heterocycle rings include those which are one ring with 5 or 6 carbon plus heteroatoms in the ring with no more than three ring heteroatoms, no more than two of which are O and S. Still more preferred are such 5- or 6-ring atom heterocycles with one or two ring atoms being O or S and the others being C; or with one, two or three ring atoms being N and the others being C. Such preferred 5- or 6-ring atom heterocycles are preferably saturated, unsaturated with one or two double bonds, or aromatic. Such preferred 5- or 6-ring atom heterocycles are preferably a single ring; or fused with a 3- to 6-ring atom hydrocarbon ring which is saturated, unsaturated with one double bond, or aromatic (phenyl); or fused with another such 5- or 6-ring atom heterocyclic ring. Heterocycles are unsubstituted or substituted. Preferred heterocycle substituents are the same as for alkyl.

As used herein unless specified otherwise, "heteroaryl" means an aromatic heterocycle.

Compounds of the Invention

The subject invention involves compounds having the following structure:

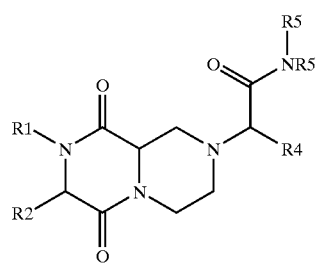

(2)

In structure 2, R1 is hydrogen or alkyl. Preferred R1 is alkyl having from 1 to about 12 carbon atoms, more preferably from 1 to about 6 carbon atoms, more preferably still 1 or 2 carbon atoms. Preferred alkyl R1 is unsubstituted or substituted; preferred substituents include aryl, heterocyclyl, amino, alkylamino, arylamino, hydroxy, alkoxy, aryloxy, thio, alkylthio, arylthio, carboxy and its esters and amides; more preferred substituents include phenyl, naphthyl, and heterocyclyl having one ring with 5 or 6 ring atoms including 1–3 heteroatoms or two fused rings with 8–10 ring atoms including 1–4 heteroatoms. More preferred R1 is hydrogen.

In structure 2, R2 is selected from hydrogen, alkyl, aryl, heterocyclyl, carboxy and its esters and amides. Alkyl R2 preferably has from 1 to about 8 carbon atoms, more preferably from 1 to about 4 carbon atoms, more preferably still 1 or 2 carbon atoms. Alkyl R2 is preferably unsubstituted or substituted; preferred substituents include aryl, heterocyclyl, amino, alkylamino, arylamino, hydroxy, alkoxy, aryloxy, thio, alkylthio, arylthio, halo, nitro, cyano, carboxy and its esters and amides; more preferred substituents include phenyl, naphthyl, heterocyclyl having one ring with 5 or 6 ring atoms including 1–3 heteroatoms or two fused rings with 8–10 ring atoms including 1–4 heteroatoms, hydroxy, $C_1$–$C_6$ alkoxy, phenoxy, thio, $C_1$–$C_6$ alkylthio, phenylthio, carboxy and its $C_1$–$C_6$ esters and amides. Aryl R2 is preferably phenyl or naphthyl, more preferably phenyl. Aryl R2 is preferably unsubstituted or substituted; preferred substituents include alkyl, aryl, heterocyclyl, amino, alkylamino, arylamino, hydroxy, alkoxy, aryloxy, thio, alkylthio, arylthio, halo, nitro, cyano, carboxy and its esters and amides; more preferred substituents include $C_1$–$C_6$ alkyl. Heterocycle R2 preferably is one ring having 5 or 6 ring atoms including 1–3 heteroatoms or two fused rings having 8–10 ring atoms including 1–4 heteroatoms. More preferred heterocycle R2 is heteroaryl. Heterocycle R2 is preferably unsubstituted or substituted; preferred substituents include alkyl, aryl, heterocyclyl, amino, alkylamino, arylamino, hydroxy, alkoxy, aryloxy, thio, alkylthio, arylthio, halo, nitro, cyano, carboxy and its esters and amides; more preferred substituents include $C_1$–$C_6$ alkyl, phenyl, naphthyl, and heterocyclyl having one ring with 5 or 6 ring atoms including 1–3 heteroatoms or two fused rings with 8–10 ring atoms including 1–4 heteroatoms.

R2 is preferably selected from known a-amino acid side-chains, especially those of α-amino acids which commonly occur in nature.

In structure 2, R1 and R2 may be attached, such attached R1/R2 being alkylene or heteroalkylene. Alkylene R1/R2 preferably has from 1 to about 6 carbon atoms, more preferably from about 2 to about 4 carbon atoms, more preferably still 3 or 4 carbon atoms. Heteroalkylene R1/R2 preferably has from 1 to about 5 carbon atoms, more preferably from 1 to about 4 carbon atoms, more preferably still 2 or 3 carbon atoms; and preferably from 1 to about 3 heteroatoms, more preferably 1 or 2 heteroatoms, more preferably still 1 heteroatom. Alkylene and heteroalkylene R1/R2 are preferably unsubstituted or substituted; preferred carbon atom substituents include alkyl, aryl, heterocyclyl, amino, alkylamino, arylamino, hydroxy, alkoxy, aryloxy, thio, alkylthio, arylthio, carboxy, and its esters and amides; more preferred carbon atom substituents include hydroxy, $C_1$–$C_6$ alkoxy, phenoxy, thio, $C_1$–$C_6$ alkylthio, phenylthio, carboxy and its $C_1$–$C_6$ esters and amides; preferred nitrogen atom substituents include $C_1$–$C_6$ alkyl (unsubstituted or substituted).

In structure 2, R4 is selected from aryl, heteroaryl, and α,β-unsaturated-conjugated aryl or heteroaryl. Aryl R4 is preferably phenyl or naphthyl, more preferably phenyl. Aryl R4 is preferably unsubstituted or substituted; preferred substituents include alkyl, aryl, alkoxy, aryloxy, alkylthio, arylthio, halo, nitro, cyano, carboxy and its esters and amides; more preferred substituents include $C_1$–$C_6$ alkyl, phenyl, $C_1$–$C_6$ alkyoxy, and halo. Heteroaryl R4 preferably is one ring having 5 or 6 ring atoms including 1–3 heteroatoms or two fused rings having 8–10 ring atoms including 1–4 heteroatoms. Heteroaryl R4 is preferably unsubstituted or substituted; preferred substituents include alkyl, aryl, alkoxy, aryloxy, alkylthio, arylthio, halo, nitro, cyano, carboxy and its esters and amides; more preferred substituents include $C_1$–$C_6$ alkyl, phenyl, $C_1$–$C_6$ alkoxy, and halo. Conjugated aryl and heteroaryl R4 preferably includes styryl. Conjugated aryl and heteroaryl R4 are preferably unsubstituted or substituted; preferred substituents include alkyl, alkoxy, aryloxy, alkylthio, arylthio, halo, nitro, cyano, carboxy and its esters and amides; more preferred substituents include $C_1$–$C_6$ alkyl, phenyl, $C_1$–$C_6$ alkoxy, and halo.

In structure 2, R5 is independently selected from hydrogen, alkyl, aryl, and heterocyclyl; or two R5 units can be taken together to form a heterocyclic ring. Alkyl R5 preferably has from 1 to about 10 carbon atoms, more preferably from 1 to about 4 carbon atoms, more preferably still 1 or 2 carbon atoms. Alkyl R5 is preferably unsubstituted or substituted; preferred substituents include alkyl, aryl, heterocyclyl, amino, alkylamino, arylamino, hydroxy, alkoxy, aryloxy, thio, alkylthio, arylthio, formyl, alkylacyl, arylacyl, halo, nitro, cyano, carboxy and its esters and amides; more preferred substituents include phenyl, naphthyl, and heterocyclyl having one ring with 5 or 6 ring atoms including 1–3 heteroatoms or two fused rings with 8–10 ring atoms including 1–4 heteroatoms. Aryl R5 is preferably phenyl or naphthyl, more preferably phenyl. Aryl R5 is preferably unsubstituted or substituted; preferred substituents include alkyl, aryl, heterocyclyl, amino, alkylamino, arylamino, hydroxy, alkoxy, aryloxy, thio, alkylthio, arylthio, formyl, alkylacyl, arylacyl, halo, nitro, cyano, carboxy and its esters and amides; more preferred substituents include $C_1$–$C_6$ alkyl, phenyl, and heterocyclyl having one ring with 5 or 6 ring atoms including 1–3 heteroatoms or two fused rings with 8–10 ring atoms including 1–4 heteroatoms. Heterocycle R5 is preferably one ring having 5 or 6 ring atoms including 1–3 heteroatoms or two fused rings having 8–10 ring atoms including 1–4 heteroatoms. More preferred heterocycle R5 is heteroaryl. Heterocycle R5 is preferably unsubstituted or substituted; preferred substituents include alkyl, aryl, heterocyclyl, amino, alkylamino, arylamino, hydroxy, alkoxy, aryloxy, thio, alkylthio, arylthio, formyl, alkylacyl, arylacyl, halo, nitro, cyano, carboxy amid its esters and amides; more preferred substituents include $C_1$–$C_6$ alkyl, phenyl, and heterocyclyl having one ring with 5 or 6 ring atoms including 1–3 heteroatoms or two fused rings with 8–10 ring atoms including 1–4 heteroatoms.

When two R5 units are taken together to form a heterocycyclic ring, preferably said ring is a ring comprising 6 atoms. A non-limiting example includes a piperazine ring wherein the 4-amino position can be substituted with one or more units described herein above, for example, benzyl.

The subject invention includes optical isomers, diasteromers, and enantiomers of the compounds of structure 2. The subject invention includes salts, hydrates, esters, amides, and imides of such compounds.

As used herein, a "salt" is a cationic salt formed at any acidic group (e.g., carboxy group), or an anionic salt formed at any basic group (e.g., amino group) on a compound of structure 2. Many salts are known. Preferred cationic salts include the alkali metal salts, such as sodium and potassium, alkaline earth metal salts, such as magnesium and calcium, and organic salts, such as ammonium. Preferred anionic salts include halides, sulfonates, carboxylates, phosphates, and the like. Salts of addition may provide an optical center where once there was none.

The compounds of the subject invention, and salts thereof, may have one or more chiral centers. The invention includes all optical isomers of the compounds of structure 2 and salts thereof, including diasteriomers and enatiomers.

The subject invention also includes libraries of compounds having structure 2. Such libraries can be mixtures of compounds of structure 2 or collections of individual compounds of structure 2.

Processes for Making the Compounds

Another aspect of the subject invention is processes for making compounds of structure 2, as generally depicted in Scheme 1.

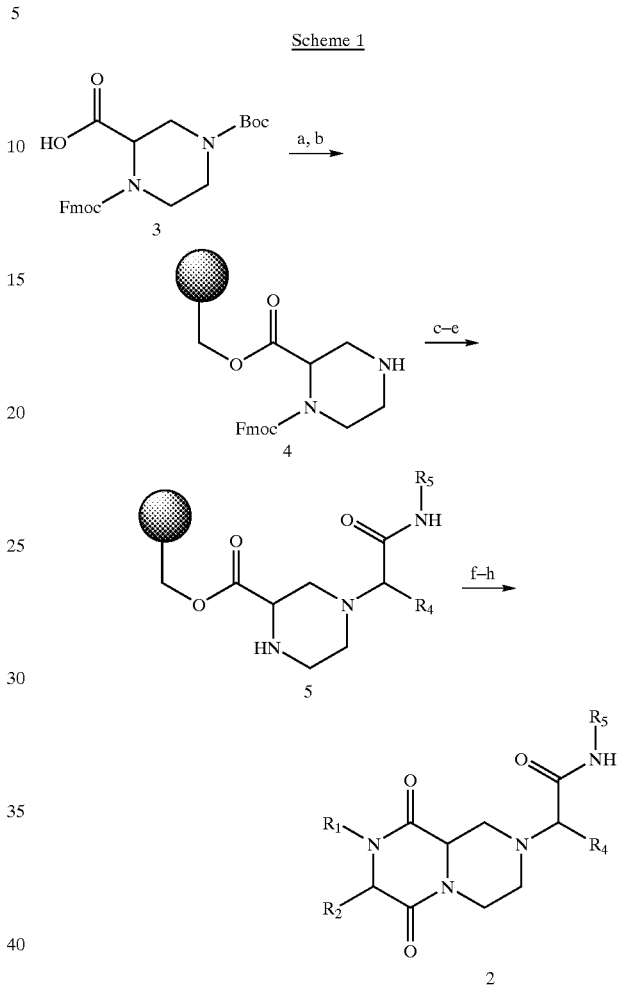

Orthogonally protected, resin bound piperazinic acid is used. Deprotection reaction is followed by functionalization of the b-nitrogen atom via the Petasis reaction. Subsequent amide bond formation leads to the desired inclusion of R4 and R5 substituents. Unblocking of the a-nitrogen, followed by Boc-N-protected a-amino acid coupling, deprotection and cyclizative cleavage, introduces the R2 and R1 substituents, and leads to bicyclic product 2.

In step a, a hydroxymethylpolystyrene resin is reacted with an orthogonally protected piperazinic acid, for example, structure 3 wherein the $N_a$ protecting group is Fmoc and the $N_b$ protecting group is Boc, to form a resin bound diprotected piperazine having the formula:

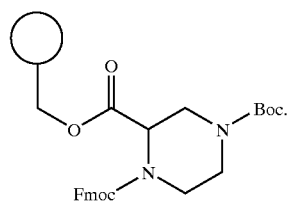

The reaction is preferably carried out, after swelling the resin in dicloromethane (DCM), in the presence of triphenylphoshine and diethyl azodicarboxylate (DEAD) in tetrahydrofuran (THF). After coupling, the resin bound diprotected piperazine is collected by filtration, washed several times using one or more solvents. Suitable solvents for washing the resin bound substrate include THF, DCM, and MeOH.

In step b, the $N_b$ protecting group is selectively removed from the resin bound diprotected piperazine to form a $N_b$ deprotected resin bound piperazine. In the example provided herein, the tert-butoxycarbonyl group is removed by reacting the resin bound diprotected piperazine with trifluoroacetic acid (TFA) in DCM, followed by washing the collected resin with one or more solvents and neutralizing the isolated $N_b$ deprotected resin bound piperazine salt to form the intermediate having the formula:

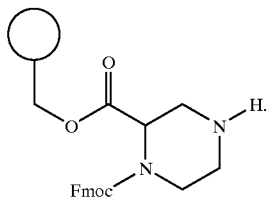

4

In step c, intermediate 4 is reacted with glyoxylic acid and a boronic acid reagent having the formula $R4\text{-}B(OH)_2$ in the presence of a solvent to form a resin bound $N_b$ alkylated piperazine having the formula:

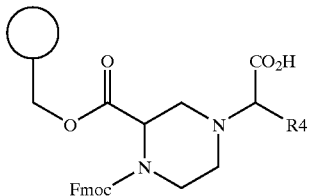

wherein said solvent is preferably DCM. Once the desired resin bound $N_b$ alkylated product is formed, the resin is isolated and washed several times with solvent. Because both the starting material and product are resin bound substrates, any unreacted starting material present can be further converted to the $N_b$ alkylated adduct by re-charging the isolated resin with additional reagents and repeating the reaction and isolation sequence.

In step d, the resin bound $N_b$ alkylated piperazine is reacted with an amine having the formula $HN(R5)_2$ to form a resin bound $N_b$ piperizine amide having the formula:

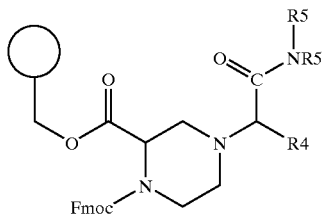

wherein the reaction takes place in the presence of a coupling reagent, for example, diisopropylcarbodiimide (DIC), and an activation catalyst, for example, 1-hydroxybenzotriazole (HOBt). The reaction is preferably conducted in the presence of a solvent, for example, dimethylformamide (DMF). After the reaction is complete, the product is isolated by filtration and washed with DMF.

In step e, the resin bound $N_b$ piperizine amide has the $N_a$ protecting group remove to form a resin bound $N_a$ amino piperizine amide. In the present illustrative example, this de-protection sequence yields a product having the formula:

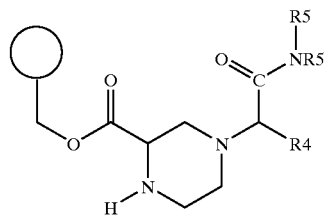

wherein the reaction is typically conducted under mild cleavage conditions. For removal of a Fmoc moiety, a 15% to 30% piperidine solution is suitable for use and the reaction is preferably conducted in DMF. The resin bound $N_a$ amino piperizine amide is collected by filtration and washed several times with solvent. As in step c, the cleavage reaction can be repeated to increase the overall product yield.

In step f, the resin bound $N_a$ amino piperizine amide is reacted with a N-protected α-amino acid in the presence of benzotriazole-1-yl-oxy-tris-pyrrolidinol-phosphonium hexafluorophosphate (PyBOP) followed by treatment with a base, for example, diisopropylethylamine (DiPEA) to form a resin bound $N_a$ amino acid coupled $N_b$ amide piperazine having the formula:

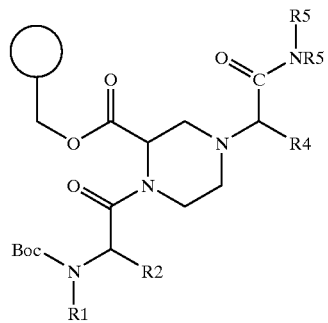

whereas in the present example a tert-butoxy carbonyl moiety is the α-amino acid protecting group. After the reaction is complete, the resin is collected and washed several times with solvent.

In step g, the protecting group of the α-amino acid moiety is removed from the $N_a$ piperazine nitrogen to yield a resin bound cyclic precursor having the formula:

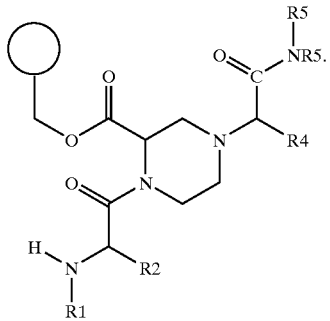

In the case when removing a Boc protecting group as exemplified herein, TFA in DCM is suitable for use. The resulting resin bound cyclic precursor is collected by filtration and washed several times with DCM and MeOH.

In step h, the resin bound cyclic precursor obtained in step g is cleaved from the hydroxymethylpolystyrene supporting resin and cyclized in the presence of an organic acid, for example, in the presence of a 5% to 20% solution of acetic acid (HOAc) in isopropanol. The cleavage/cyclization is accomplished at a temperature of from about 30° C. to about 80° C. for about 20 hours to about 80 hours. The resin is removed by filtration and the product having the formula:

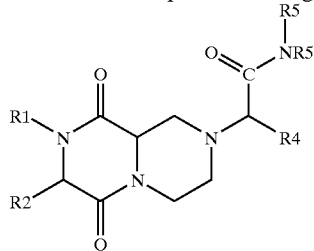

is isolated by concentrating the filtrate in vacuo. The product thus obtained is preferably purified by co-evaporating it several times with chloroform, and then drying under vacuum.

The following non-limiting examples illustrate, in more detail, processes of the subject invention.

EXAMPLE 1 a) Hydroxymethylpolystyrene resin (1.0 g, 1.44 mmol/g, Advanced Chemtech) is swelled in anhydrous dichloromethane (DCM) (6 mL). Triphenylphosphine ($Ph_3P$) (1.13 g, 4.32 mmole) is dissolved in this slurry and the heterogeneous reaction is cooled to 0° C. under nitrogen. To this gently stirring slurry is added a tetrahydrofuran (THF) (30 mL) solution of $N_\alpha$-Fmoc-$N_\beta$-Boc-2-carboxypiperazine 3 (1.95 g, 4.32 mmol) and diethylazodicarboxylate (DEAD) (751 mL, 4.32 mmole) over a period of 30 minutes. The reaction is allowed to stir for 72 h, at which point the resin is filtered and washed with THF (3×), DCM (3×), MeOH (3×), then multiple, successive and alternating DCM and MeOH washes (standard manner).

b) Piperazinic resin ester from step a (1.4 g) is swelled in DCM, filtered and treated with a 40% solution of trifluoroacetic acid (TFA) in DCM for 1 h. The resin is filtered and washed with DCM (3×), MeOH (3×), then alternating DCM/MEOH as in (a). The resin bound amine TFA salt is then neutralized with a 10% solution of diisopropylethylamine (DiPEA) in DCM and re-washed in the standard manner.

c) The resin ester 4 from step b is swelled in DCM (10 mL) and to this is added glyoxylic acid (265 g, 2.88 mmol) and a boronic acid (2.88 mmol) as a solution in MeOH (15 mL). The resulting slurry is agitated for 5 h, before filtering the resin and washing with MeOH (3×). The above procedure is repeated again for 16 h, after which the resin is again filtered and washed in the standard manner.

d) The resin ester from step c is swelled in DMF (5 ml) and to this is added hydroxybenzotriazole (HOBt) (1.10 g, 7.2 mmol) followed by diisopropylcarbodiimide (DIC) (907 mg, 7.2 mmol). The reaction is agitated for 3 h, after which the resin is washed with dimethylformamide (DMF) (4×). The resin is swelled again in DMF (10 ml), and to this slurry is added an amine (7.2 mmol). The reaction is allowed to agitate for 15 h. The resin is filtered and washed with DMF (3×) followed by the standard manner wash.

e) The resin ester from step d is treated with 25% piperidine in DMF for 20 min. The resin is filtered and rinsed with DMF (2X) before repeating. The resin product is filtered and washed in the standard manner.

f) The resin product 5 from step e is swelled in DMF. To this is added a boc-α-amino acid (Boc-AA) (7.2 mmole), benzotriazol-1-yl-oxy-tris-pyrrolidino-phosphonium hexafluorophosphate (PyBOP) (3.74 g, 7.2 mmole) followed by DiPEA (1.11 g, 8.64 mmole). The reaction is agitated for 5 h, filtered and rinsed with DMF (3×) in the standard manner.

g) The resin product from step f is treated with 25% TFA/DCM for 1 h. The resin is filtered and washed.

h) The resin product from step g is taken up in 10% acetic acid in isopropanol (AcOH/iPrOH) and heated for 16 h at 50° C. The resin is filtered off and washed several times using MeOH. The filtrate and washings are combined and concentrated to give an off white solid. The solid as co-evaporated several times using chloroform before being dried under vacuum for 15 h.

EXAMPLES 2–7

The following non-limiting exemplary compounds are made using the process of Example 1 by reacting the indicated boronic acids, amines, and boc-α-amino acids therein:

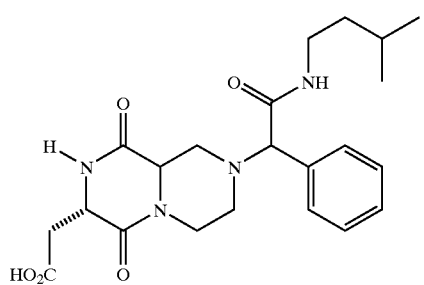

2a

-continued
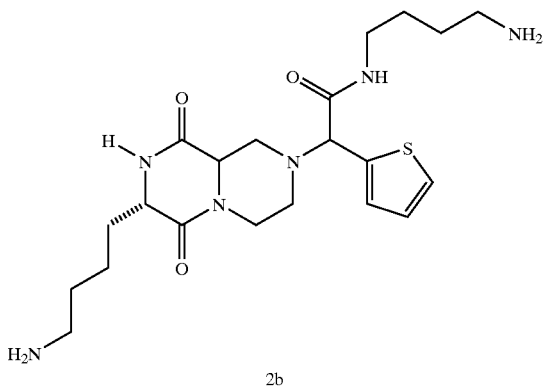
2b
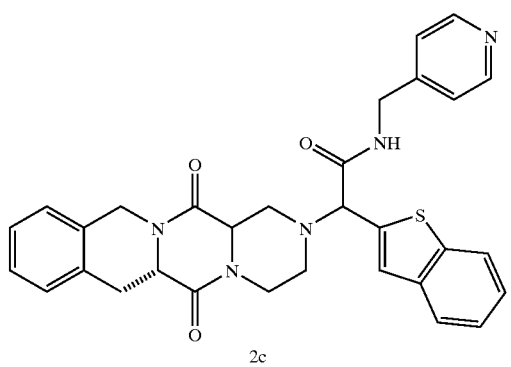
2c
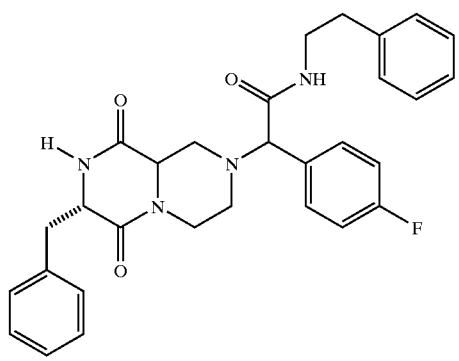
2d
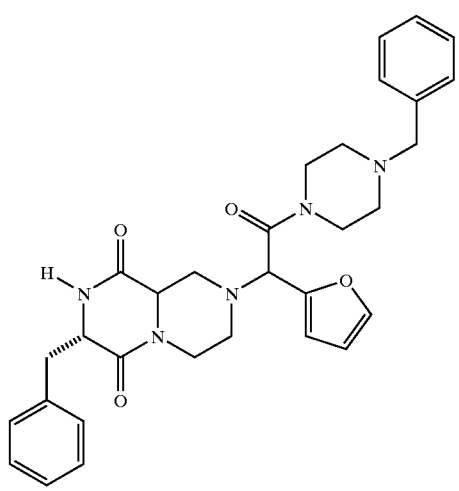
2e

-continued

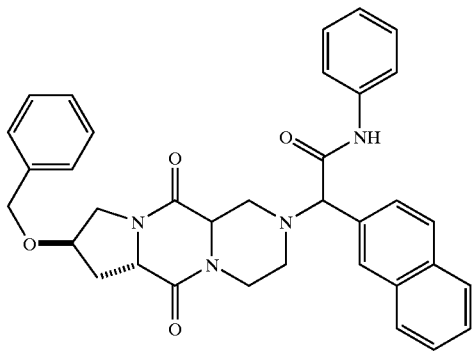

2f

| Example | Boronic Acid | Amine | Amino Acid | Product |
|---|---|---|---|---|
| 2 | phenylboronic acid | isoamylamine | Boc-Asp (O-tBu)-OH | 2a |
| 3 | 2-thiopheneboronic acid | mono-Boc-butyl-1,4-diamine | Boc-Lys(Boc)-OH | 2b |
| 4 | benzothiophene-2-bornonic acid | 4-aminomethyl-pyridine | Boc-Tic-OH | 2c |
| 5 | 4-fluoroboronic acid | phenethylamine | Boc-Phe-OH | 2d |
| 6 | 2-furylboronic acid | benzylamine | Boc-Phe-OH | 2e |
| 7 | 2-naphthylboronic acid | aniline | Boc-Hyp(OBn)-OH | 2f |

The above processes of the subject invention are carried out using solid-support resin. This makes reaction separation and purification of intermediates and final product amenable to automation. Libraries of compounds of structure 2 are readily prepared using the subject invention processes. Automation of the preparation of such libraries is achieved using equipment known to the skilled combinatorial chemist. Such equipment can be used to make libraries which are mixtures of compounds of structure 2 or collections of individual compounds of structure 2 each in an isolated well.

While particular embodiments of the subject invention have been described, it will be obvious to those skilled in the arts that various changes and modifications of the subject invention can be made without departing from the spirit and scope of the invention. It is intended to cover, in the appended claims, all such modifications that are within the scope of this invention.

What is claimed is:

1. A compound including all enatiomeric and diasteriomeric forms and pharmaceutically acceptable salts thereof, having the formula:

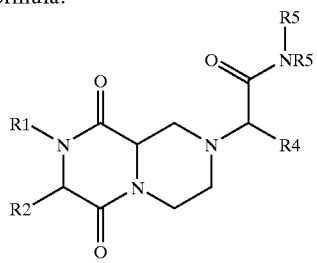

wherein:
a) R1 is hydrogen or substituted or unsubstituted alkyl;
b) R2 is selected from the group consisting of hydrogen, alkyl, aryl, heterocyclyl, a unit which comprises a carboxylic acid, ester, or amide moiety;
c) R1 and R2 can be taken together to form one or two saturated or unsaturated fused rings said rings comprising from 5 to 10 carbon atoms, 1 to 4 heteroatoms, and mixtures thereof;
d) R4 is selected from the group consisting of aryl, heteroaryl, and units comprising a double bond in conjugation with said aryl or heteroaryl units;
e) R5 is selected from the group consisting of hydrogen, alkyl, aryl, and heterocyclyl; or two R5 units can be taken together to form a heterocyclic ring.

2. A compound according to claim 1 wherein R1 is hydrogen or $C_1$–$C_{12}$ alkyl.

3. A compound according to claim 2 wherein R1 is hydrogen of $C_1$–$C_6$ alkyl.

4. A compound according to claim 3 wherein R1 is hydrogen.

5. A compound according to claim 1 wherein R1 is a substituted alkyl unit, said substitution comprising an aryl or heterocyclyl moiety.

6. A compound according to claim 5 wherein said substituted alkyl unit comprises phenyl or naphthyl.

7. A compound according to claim 1 wherein R2 is hydrogen or $C_1$–$C_8$ alkyl.

8. A compound according to claim 1 wherein R1 and R2 are taken together to form a fused ring said ring comprising from 5 to 6 carbon atoms or a ring comprising 1 to 4 heteroatoms, and mixtures thereof.

9. A compound according to claim 8 wherein R1 and R2 are taken together to form an aryl fused ring having the formula:

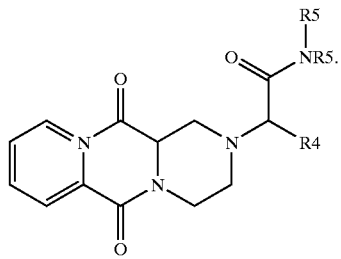

10. A compound according to claim 8 wherein R1 and R2 are taken together to form two fused rings having the formula:

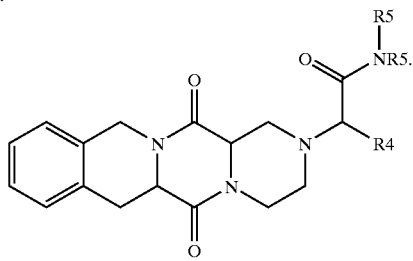

11. A compound according to claim 1 wherein R4 is selected from the group consisting of phenyl, naphthyl, styryl, and heteroaryl comprising one ring having from 5 to 10 carbon atoms, 1 to 4 heteroatoms, and mixtures thereof.

12. A compound according to claim 1 wherein R4 is furanyl, thienyl, or benzothienyl.

13. A compound according to claim 1 wherein R5 is selected from the group consisting of phenyl, naphthyl, styryl, and heteroaryl comprising one ring having from 5 to 6 carbon atoms, 1 to 4 heteroatoms, and mixtures thereof.

14. A compound according to claim 1 wherein two R5 units are taken together to form a 4-N substituted piperazine ring.

15. A process for preparing a peptide β-turn mimetic compound including all enatiomeric and diasteriomeric forms and pharmaceutically acceptable salts thereof, said compound having the formula:

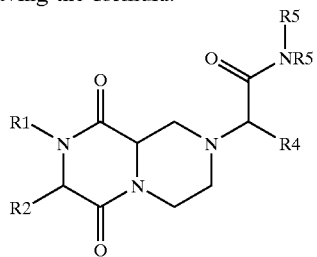

wherein:
a) R1 is hydrogen or substituted or unsubstituted alkyl;
b) R1 is selected from the group consisting of hydrogen, alkyl, aryl, heterocyclyl, a unit which comprises a carboxylic acid, ester, or amide moiety;
c) R1 and R2 can be taken together to form one or two saturated or unsaturated fused rings said rings comprising from 5 to 10 carbon atoms, 1 to 4 heteroatoms, and mixtures thereof;
d) R4 is selected from the group consisting of aryl, heteroaryl, and units comprising a double bond in conjugation with said aryl or heteroaryl units;
e) R5 is selected from the group consisting of hydrogen, alkyl, aryl, and heterocyclyl; or two R5 units can be taken together to form a heterocyclic ring;

said process comprising the steps:
a) reacting an orthogonally protected piperazinic acid with a resin to form resin bound diprotected piperazine having the formula:

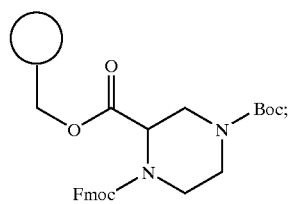

b) removing selectively the the $N_b$ protecting group from the resin bound deprotected piperazine and neutralizing the isolated $N_b$ deprotected resin bound piperazine salt to form the intermediate having the formula:

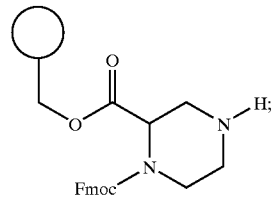

c) reacting said $N_b$ deprotected resin bound piperazine with glyoxylic acid and a boronic acid reagent having the formula $R4\text{-}B(OH)_2$ in the presence of a solvent to form a resin bound $N_b$ alkylated piperazine having the formula:

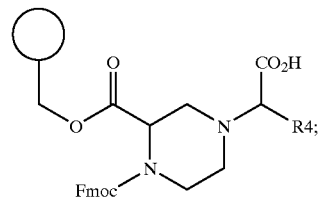

d) reacting said resin bound $N_b$ alkylated piperazine with an amine having the formula $HN(R5)_2$ to form a resin bound $N_b$ piperizine amide having the formula:

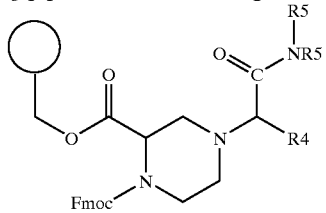

in the presence of an coupling reagent, an activation catalyst, and dimethylformamide;

e) reacting said resin bound $N_b$ piperizine amide with a 15% to 30% piperidine solution in DMF to form a resin bound $N_a$ amino piperazine amide having the formula

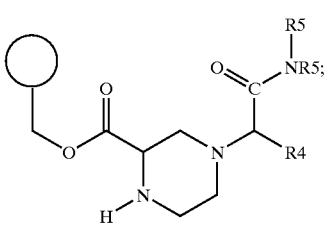

f) reacting said resin bound $N_a$ amino piperizine amide with a N-protected α-amino acid in the presence of benzotriazole-1-yl-oxy-tris-pyrrolidinol-phosphonium hexafluorophosphate and a base to form a resin bound $N_a$ amino acid coupled $N_b$ amide piperazine having the formula:

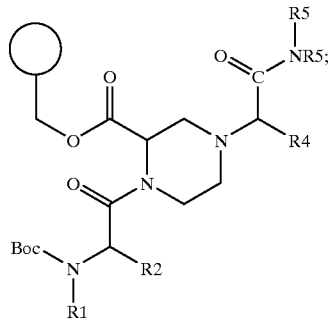

g) reacting said a resin bound $N_a$ amino acid coupled $N_b$ amide piperazine with trifluoroacetic acid in dichloromethane to form a resin bound cyclic precursor having the formula:

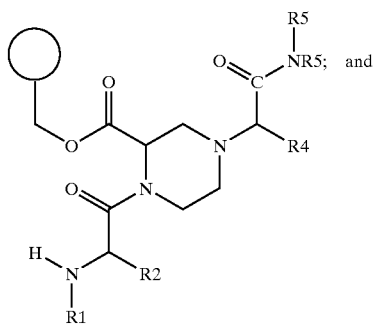

h) reacting said resin bound cyclic precursor with a 5% to 20% solution of acetic acid (HOAc) in isopropanol to cleave said cyclic precursor from said resin and heating said precursor at a temperature of from about 30° C. to about 80° C. for about 20 hours to about 80 hours thereby cyclizing said precursor to form a peptide β-turn mimetic.

* * * * *